(12) United States Patent
McKinnon

(10) Patent No.: US 11,980,746 B2
(45) Date of Patent: May 14, 2024

(54) SELF-PUMPING SYRINGE

(71) Applicant: Becton, Dickinson and Company, Franklin Lakes, NJ (US)

(72) Inventor: Austin Jason McKinnon, Herriman, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 123 days.

(21) Appl. No.: 16/382,383

(22) Filed: Apr. 12, 2019

(65) Prior Publication Data

US 2019/0321556 A1 Oct. 24, 2019

Related U.S. Application Data

(60) Provisional application No. 62/659,879, filed on Apr. 19, 2018.

(51) Int. Cl.
*A61M 5/31* (2006.01)
*A61M 5/315* (2006.01)
(Continued)

(52) U.S. Cl.
CPC ...... *A61M 5/31511* (2013.01); *A61M 5/3129* (2013.01); *A61M 5/31528* (2013.01);
(Continued)

(58) Field of Classification Search
CPC ............ A61M 5/31511; A61M 5/3129; A61M 5/31528; A61M 5/31533; A61M 5/502;
(Continued)

(56) References Cited

U.S. PATENT DOCUMENTS 6,010,485 A * 1/2000 Buch-Rasmussen ........................
A61M 5/204
604/248
9,222,470 B2 * 12/2015 Genoud ............ A61M 5/16831
(Continued)

FOREIGN PATENT DOCUMENTS

CH 688224 A5 6/1997
CN 103347553 A 10/2013
(Continued)

OTHER PUBLICATIONS

Werner, Herb. Valveless Piston Pumps Complete Denitrification of Effluent Wastewater. Sep. 3, 2015. Pumps & Systems. Sep. 2015 Issue <<https://www.pumpsandsystems.com/valveless-piston-pumps-complete-denitrification-effluent-wastewater >> (Year: 2015).*

*Primary Examiner* — William R Carpenter
(74) *Attorney, Agent, or Firm* — The Webb Law Firm

(57) ABSTRACT

A syringe is provided. The syringe includes a syringe barrel including an open proximal end, a closed distal end, and a sidewall extending therebetween. The syringe also includes: a plunger having an annular sidewall configured to seal against an interior surface of the sidewall of the syringe barrel, the plunger being configured to move through the syringe barrel in proximal and distal directions; a pump in fluid communication with an interior volume of the syringe barrel, the pump being configured to draw fluid from the syringe barrel; and a nozzle including a lumen in fluid communication with the pump and configured to receive fluid drawn from the syringe barrel by the pump and to expel the fluid through a distal end of the lumen. The pump can be a valve-less piston pump.

14 Claims, 8 Drawing Sheets

(51) Int. Cl.
*A61M 5/32* (2006.01)
*A61M 5/50* (2006.01)

(52) U.S. Cl.
CPC ....... *A61M 5/31533* (2013.01); *A61M 5/3221* (2013.01); *A61M 5/502* (2013.01)

(58) Field of Classification Search
CPC .... A61M 5/3221; A61M 5/1452; A61M 5/19; A61M 5/5013; A61M 39/10; A61M 5/16809; A61M 5/14216; A61M 5/14212; A61M 5/31593; A61M 5/31565; F04B 7/06
See application file for complete search history.

(56) References Cited

U.S. PATENT DOCUMENTS

| | | | |
|---|---|---|---|
| 9,402,961 | B2 | 8/2016 | Leak et al. |
| 10,132,308 | B2 | 11/2018 | Focht et al. |
| 10,258,749 | B2 | 4/2019 | Schoonmaker et al. |
| 10,954,928 | B2 * | 3/2021 | Burli ........................ F04B 7/06 |
| 2007/0237658 | A1 * | 10/2007 | Burns ........................ F04B 7/06 417/417 |
| 2010/0305508 | A1 * | 12/2010 | Franks ................... F16K 11/085 604/152 |
| 2011/0144568 | A1 * | 6/2011 | Melsheimer .......... A61M 37/00 604/24 |
| 2014/0276411 | A1 * | 9/2014 | Cowan ................... A61B 6/481 604/143 |
| 2015/0265775 | A1 | 9/2015 | Cowe |
| 2016/0121043 | A1 | 5/2016 | Weibel |
| 2016/0121095 | A1 * | 5/2016 | Maurice, Jr. .......... A61M 39/24 604/247 |
| 2016/0151559 | A1 * | 6/2016 | Cowan ................. A61M 5/2053 600/432 |
| 2020/0309104 | A1 * | 10/2020 | Bürli ........................ F04B 7/06 |

FOREIGN PATENT DOCUMENTS

| | | |
|---|---|---|
| JP | 2001501504 A | 2/2001 |
| JP | 2012511392 A | 5/2012 |
| JP | 2017513577 A | 6/2017 |
| WO | 9320864 A1 | 10/1993 |
| WO | 2009069063 A1 | 6/2009 |
| WO | WO-2015157174 A1 * | 10/2015 .......... A61M 5/1413 |
| WO | WO-2017211851 A2 * | 12/2017 ........ A61M 5/14248 |

\* cited by examiner

SELF-PUMPING SYRINGE

CROSS-REFERENCE TO RELATED APPLICATION

The present invention claims priority to U.S. Provisional Application Ser. No. 62/659,879 entitled "Self-Pumping Syringe" filed Apr. 19, 2018, the entire disclosure of which is hereby incorporated by reference in its entirety.

BACKGROUND

Field of the Invention

This invention relates generally to a syringe assembly and, more particularly, to a syringe assembly including a rotary piston pump configured to draw fluid from the syringe in precise volumes.

Description of Related Art

During use of a conventional syringe assembly including a syringe barrel, fluid is drawn into the syringe barrel through a distal tip, nozzle, or needle thereof, by moving a plunger rod and plunger or stopper through a syringe barrel in a proximal direction, thereby drawing the fluid into the barrel. The process of drawing fluid into the syringe barrel is known as aspiration. Following aspiration, to perform an injection, fluid is driven from the syringe barrel by pushing the plunger and plunger rod back through the syringe barrel in the distal direction. Injection volume is controlled by observing the position of the plunger and/or plunger rod within the syringe barrel and/or the distance traveled by the plunger within the barrel during the injection. Such injections may be performed manually (e.g., by grasping the proximal end of the plunger rod and manually pushing the plunger rod in the distal direction) or automatically with a syringe pump (e.g., a syringe pump having a linear actuator for automatically advancing the plunger rod and/or plunger through the syringe barrel).

Precisely controlling movement of the plunger through the syringe barrel and the resulting injection volume can be difficult due to friction and break-loose forces between the plunger and interior sidewall of the syringe barrel. For example, precisely controlling delivery of small fluid volumes from a syringe is made difficult due to static friction or stiction forces between the syringe barrel and plunger. Stiction refers to static friction that needs to be overcome to enable relative motion of stationary objects in contact, such as the plunger and the interior sidewall of the syringe barrel. As a result of the stiction forces, movement of the plunger through the barrel tends to be jerky or inconsistent since, after the static friction forces holding the plunger against the syringe barrel sidewall are overcome, the plunger may jerk or push forward through the barrel. The jerky movement means that fluid is not delivered from the syringe barrel at a constant rate, which makes controlling fluid delivery volume imprecise. Previously, syringe stiction reduction has typically been considered for ergonomic reasons, but also because it introduces a noise factor into the accuracy of conventional syringe pumps. Stiction control or reduction is typically approached in the context of lubricants or stopper design.

However, there is a need in the art for improved solutions for addressing stiction and for enabling delivery of precise volumes of fluid from a syringe barrel. Desirably, such solutions would be based on the mechanical configuration of the syringe assembly or syringe pump drive unit and would not require including additional lubricants or coatings on the plunger or stopper. The syringe assembly, fluid delivery system, and methods disclosed herein are intended to address these issues.

SUMMARY

The present disclosure is directed to a syringe and syringe assembly including a pump for drawing a precise fluid volume from the syringe.

According to an aspect of the disclosure, a syringe includes: a syringe barrel having an open proximal end, a closed distal end, and a sidewall extending therebetween; a plunger having an annular sidewall configured to seal against an interior surface of the sidewall of the syringe barrel, the plunger being configured to move through the syringe barrel in proximal and distal directions; a rotary piston pump in fluid communication with an interior volume of the syringe barrel configured to draw fluid from the syringe barrel by rotation of a piston; and a nozzle. The nozzle includes a lumen in fluid communication with the rotary piston pump configured to receive fluid drawn from the syringe barrel by the pump and to expel the fluid through a distal end of the lumen.

In some examples, the rotary piston pump is a rotary valve-less piston pump. A rotary valve-less piston pump can include an annular body having an open proximal end and a closed distal end, which define a cavity. The cavity can be in fluid communication with the interior volume of the syringe barrel and the lumen of the nozzle. The piston can be slidably and rotatably inserted in the cavity. When the piston is in a partially retracted position, fluid flow between the lumen of the nozzle and the interior volume of the syringe barrel through the cavity of the pump can be permitted, and fluid flow through the open proximal end of the annular body can be prevented. Movement of the piston in an axial direction into the cavity from the partially retracted position can cause the piston to seal at least one of the lumen of the nozzle or the interior volume of the syringe barrel, such that fluid communication between the cavity and the nozzle and/or the syringe barrel is prevented.

In some examples, during a piston stroke, the piston rotates 360 degrees and moves axially through the cavity between a seated position, a suction position, and back to the seated position. In the suction position, fluid can be drawn from the interior of the syringe barrel into the cavity. In the seated position, fluid can be expelled from the cavity through the lumen of the nozzle. A fluid volume expelled from the cavity through the lumen during each piston stroke may be from about 5 mL to 100 mL.

In some examples, the annular body includes at least one annular seal extending from an interior sidewall thereof, the seal being configured to prevent fluid from leaking from the open proximal end of the annular body. Optionally, the nozzle further includes a male luer connector configured to connect to a female luer connector of another fluid delivery device to establish fluid communication between the syringe and the fluid delivery device. Alternatively, the nozzle can include a threaded connector comprising an annular body having threads on an interior surface thereof.

In some examples, the pump is integrally molded to the syringe barrel. The pump can also be removably connected to the syringe barrel.

According to another aspect of the disclosure, a syringe assembly for delivery of a fluid, includes: a syringe having a syringe barrel having an open proximal end, a closed distal end, and a sidewall extending therebetween; a plunger disposed in the syringe barrel having an annular sidewall configured to seal an interior surface of the sidewall of the syringe barrel and configured to move through the syringe barrel in the proximal and distal directions; and a nozzle extending from the distal end of the syringe barrel having a lumen in fluid communication with an interior volume of the syringe barrel. The syringe assembly also includes a pump assembly removably connected to the nozzle of the syringe barrel in fluid communication with the interior volume of the syringe barrel. The pump assembly can include a rotary piston pump configured to draw fluid from the interior volume of the syringe barrel through an inflow port of the pump assembly and to expel the received fluid from an outflow port thereof by rotational movement of a piston.

In some examples, the rotary piston pump is a rotary valve-less piston pump having an annular body having an open proximal end and a closed distal end, which define a cavity. The piston can be slidably and rotatably inserted in the cavity. In some examples, fluid is drawn from the interior volume of the syringe barrel into the cavity through the inflow port and is expelled from the cavity through the outflow port.

In some examples, the piston is in a partially retracted position, fluid flow between the inflow port and the outflow port through the cavity of the pump assembly is permitted, and fluid flow through the open proximal end of the annular body is prevented. Movement of the piston in an axial direction from the partially retracted position into the cavity causes the piston to seal at least one of the inflow port or the outflow port, such that fluid communication between the cavity and the inflow port and/or the outflow port is prevented. During a piston stroke, the piston may rotate 360 degrees and move axially through the cavity between a seated position, a suction position, and back to the seated position.

According to another aspect of the disclosure, a fluid delivery system includes a syringe and a drive unit. The syringe includes: a syringe barrel having an open proximal end, a closed distal end, and a sidewall extending therebetween; a plunger having an annular sidewall configured to seal against an interior surface of the sidewall of the syringe barrel and configured to move through the syringe barrel in proximal and distal directions; a rotary piston pump in fluid communication with an interior volume of the syringe barrel configured to draw fluid from the syringe barrel by rotational movement of a piston; and a nozzle. The nozzle includes a lumen in fluid communication with the pump and configured to receive fluid drawn from the syringe barrel by the pump and to expel the fluid through a distal end of the lumen. The drive unit is connected to the pump for actuating the pump to draw fluid from the interior volume of the syringe barrel.

In some examples, the rotary piston pump is a rotary valve-less piston pump. The rotary valve-less piston pump can include an annular body having an open proximal end and a closed distal end, which define a cavity. The cavity is in fluid communication with the interior volume of the syringe barrel and the lumen of the nozzle. The piston can be slidably and rotatably disposed within the cavity.

In some examples, the drive unit is removably connected to the piston and configured to move the piston through a piston stroke in which the piston rotates 360 degrees and moves axially through the cavity between a seated position, a suction position, and back to the seated position. The drive unit can include a rotating shaft and a cam connected to the piston.

According to another aspect of the disclosure, a method of dispensing fluid from a syringe is disclosed. The syringe includes a syringe barrel having an open proximal end, a closed distal end, and a sidewall extending therebetween; a plunger including an annular sidewall configured to seal an interior surface of the sidewall of the syringe barrel and configured to move through the syringe barrel in the proximal and distal directions; and a rotary piston pump in fluid communication with an interior volume of the syringe barrel. The rotary piston pump can be configured to draw fluid from the syringe barrel by rotational movement of a piston. The syringe can also include a nozzle having a lumen in fluid communication with the pump and configured to receive fluid drawn from the syringe barrel by the pump and to expel the fluid through a distal end of the lumen. The method for dispensing fluid from the syringe can include: filling the syringe by drawing fluid through the nozzle and into the syringe barrel, while the piston of the rotary piston pump is in a partially retracted position; and after the syringe is at least partially filled, actuating the pump to cause the piston to move through at least one piston stroke. The at least one piston stroke can include simultaneously rotating the piston 360 degrees and moving the piston axially through a cavity from a seated position, to a suction position, and back to the seated position to draw a volume of fluid from the syringe barrel into the cavity and to expel the volume of fluid from the syringe through the nozzle.

In some examples, the rotary piston pump is a rotary valve-less piston pump. The rotary piston pump can be moved through the at least one piston stroke automatically by a drive unit. Actuating the rotary piston pump can include performing multiple piston strokes to expel multiple discrete volumes of fluid from the syringe through the nozzle.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DETAILED DESCRIPTION

Figure 1:
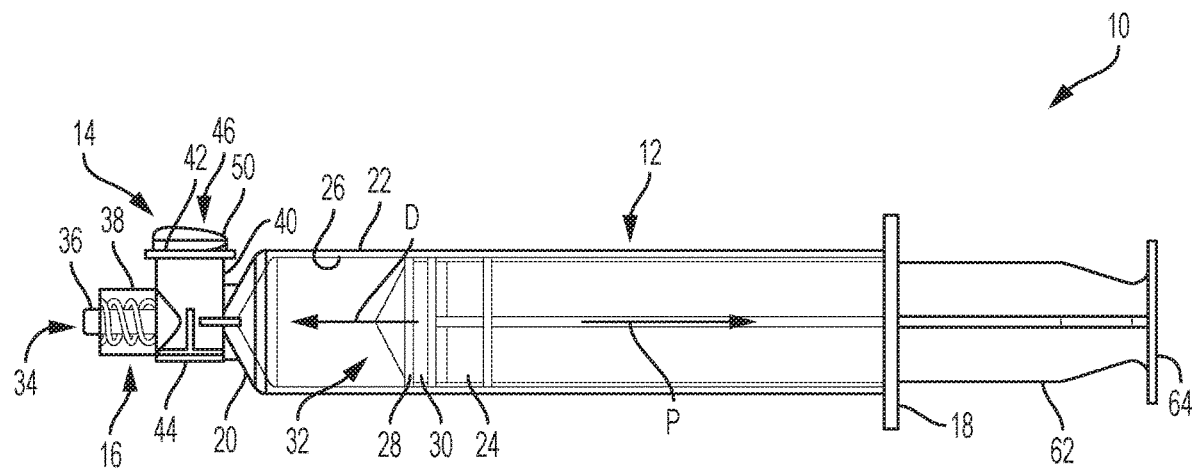
FIG. 1 is a side view of a syringe including a pump according to an aspect of the disclosure.
Figure 2:
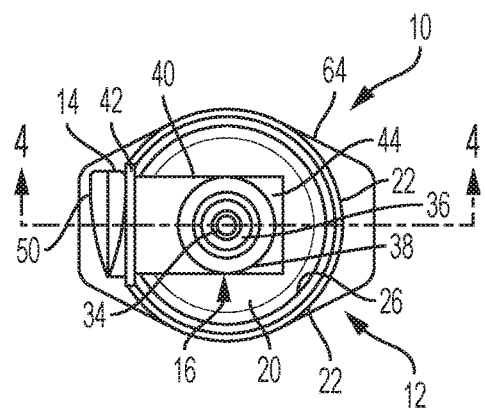
FIG. 2 is a bottom view of the syringe of FIG. 1.
Figure 3:
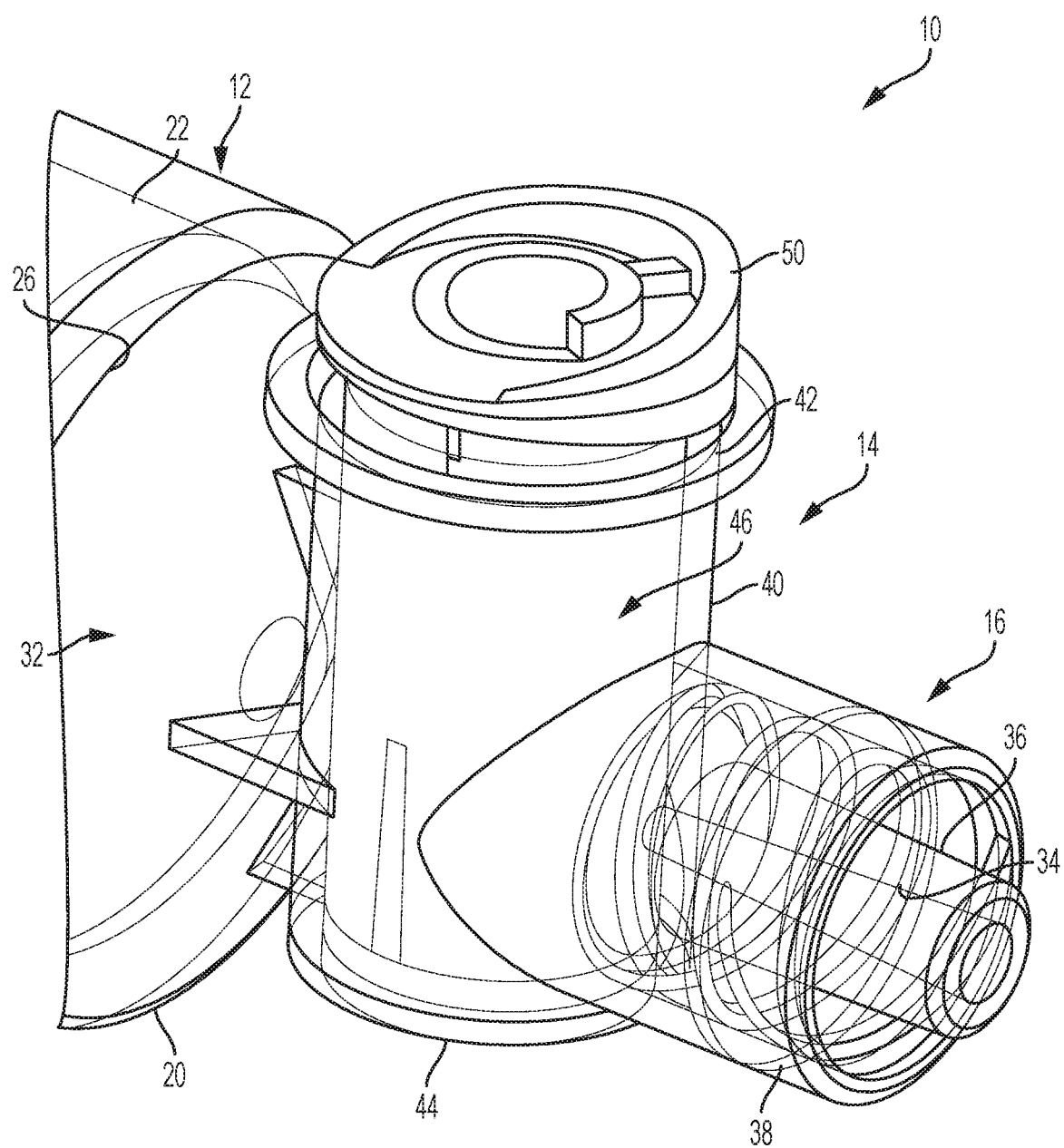
FIG. 3 is a perspective view of a portion of the pump of the syringe of FIG. 1.

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. The term "proximal" refers to a portion of a structure nearest to the center of the structure or to a point of attachment or actuation of the structure. For example, a "proximal portion" of a syringe is the portion of the syringe configured to be grasped by a user. The term "distal" refers to a portion of a structure farthest away from the center or from the point of attachment or actuation of the structure (e.g., the portion of the structure opposite from the proximal portion). For example, a "distal portion" of a syringe is the end of the syringe including the needle or nozzle. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

According to an aspect of the disclosure, a syringe including a pump for drawing a precise volume of fluid from the syringe is provided. The pump can be a rotary valve-less piston pump. The syringe can be used, for example, for extracting fluid from a fluid container, such as a vial, to fill or partially fill the syringe. The filled or partially filled syringe can then be coupled to a drive unit for fluid delivery of a volume of the fluid to a patient. In other examples, the fluid can be expelled from the syringe to an IV bag for later infusion. As described herein, the syringe can be used as a conventional syringe. The syringe can be quickly converted from a conventional syringe to a precision syringe pump merely by attaching a drive unit to the pump to advance and retract the pump piston. Desirably, addition of the pump to a conventional syringe design only increases manufacturing costs for the syringe by a small amount. In some cases, the drive unit can be reusable, so that the cost of the drive unit can be amortized over many injections. In some examples, the pump is integrated directly into the syringe. In other examples, a pump assembly can be removably connected to a distal nozzle of a conventional syringe to form a syringe assembly capable of delivering precise fluid volumes.

According to another aspect of the disclosure, the syringe and pump can be integrated into a fluid dispensing system including the drive unit. For example, the drive unit may be configured to connect to the piston of the pump and to drive the piston back and forth. Driving of the piston through the pump draws fluid from an interior volume of the syringe and expels the fluid from the syringe. The drive unit can be configured to repeatedly retract and advance the piston to expel multiple precise volumes of fluid from the syringe.

Syringe and Pump

Figure 8:
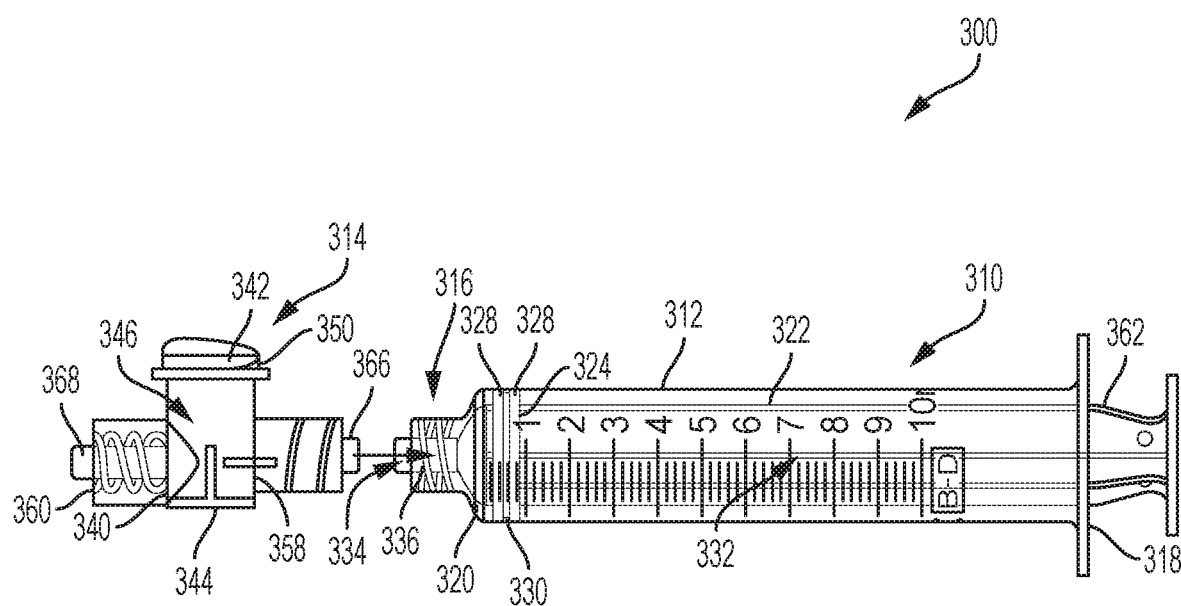
FIG. 8 is a side view of a syringe assembly including a syringe and removable pump assembly according to another aspect of the disclosure.

A syringe 10 including a syringe barrel 12, a pump 14, and a nozzle 16 is shown in FIGS. 1-4D. In some examples, as shown in FIGS. 1-4D, the syringe barrel 12, pump 14, and nozzle 16 are integrally formed. In other examples, as shown in FIG. 8, the pump 14 and nozzle 16 are removably connected to the syringe barrel 12. The pump 14 is in fluid communication with an interior volume 32 of the syringe barrel 12 and is configured to draw fluid from the syringe barrel 12 and to expel fluid through the nozzle 16.

As shown in FIG. 1, the syringe barrel 12 includes an open proximal end 18, a closed distal end 20, and a sidewall 22 extending therebetween. The syringe barrel 12, as well as portions of the pump 14 and nozzle 16, can be formed from a suitable hard, rigid biocompatible material, such as plastic, glass, or metal. For example, a syringe barrel 12 can be formed from clear polycarbonate, so that the fluid contents in the barrel 12 can be observed. The syringe 10 also includes a stopper or plunger 24 configured to seal against an interior surface 26 of the sidewall 22 of the syringe barrel 12. For example, the plunger 24 can include an annular seal 28 extending around an annular sidewall 30, such as an elastomeric annular seal, of the plunger 24. In other examples, the sidewall 30 can include various ridges, protrusions, or fins for creating a suitable seal between the plunger 24 and sidewall 22 of the syringe barrel 12. The plunger 24 is configured to move through the syringe barrel 12 in a proximal direction (shown by arrow P in FIG. 1) and distal direction (shown by arrow D in FIG. 1). In some examples, as is known in the art, a plunger rod 62 may be removably mounted or integrally formed with a proximal portion of the plunger 24. The plunger rod 62 can be an elongated structure including a latching mechanism (not shown) for connection with the plunger 24. The plunger rod 62 may also include a circular disk or flange 64 extending from a proximal end thereof.

Figure 4A:
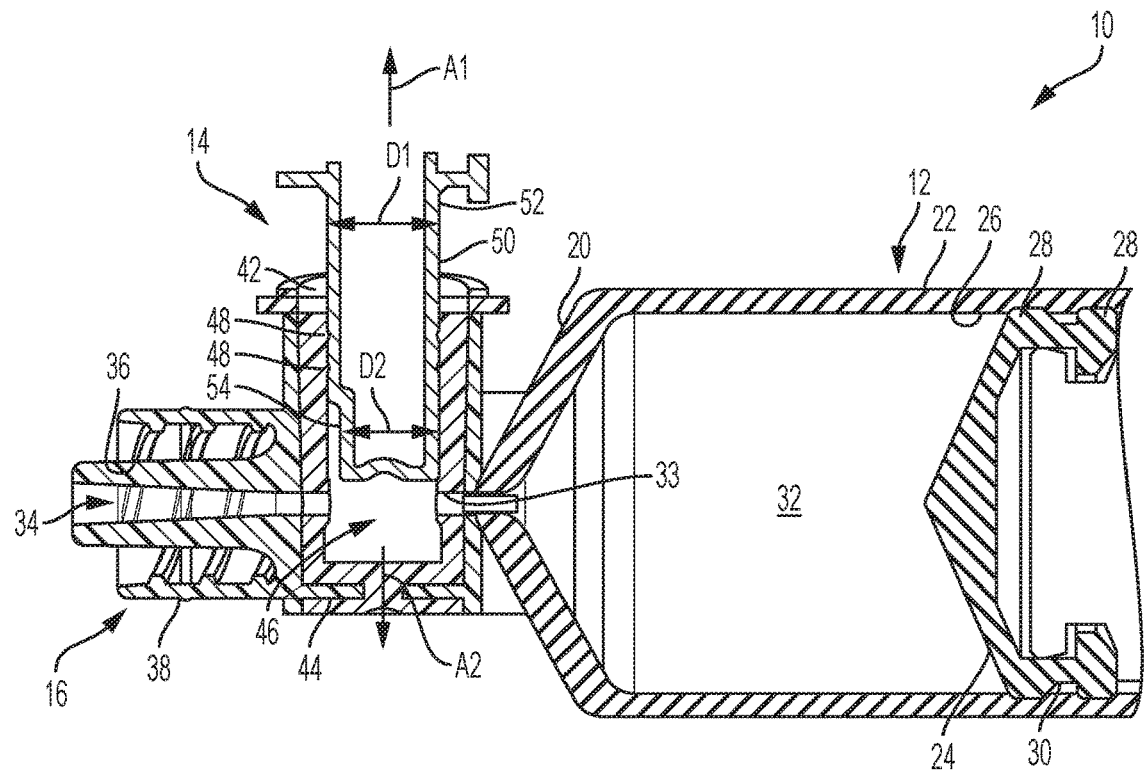
FIG. 4A is a cross-sectional view of a portion of the syringe of FIG. 1 taken along line 4-4 (shown in FIG. 2) in a partially retracted position according to an aspect of the disclosure.

In some examples, the nozzle 16 includes a central channel or lumen 34 in fluid communication with the pump 14 configured to receive fluid drawn from the syringe barrel 12 and through the pump 14. The lumen 34 can have an inner diameter of about 1.5 mm. In some instances, the lumen 34 can be necked down to a minimum inner diameter of about 0.5 mm to 0.8 mm. The narrowest portion of the lumen 34 may be positioned where the lumen 34 meets the pump 14, as shown in FIGS. 4A-5. The fluid is expelled from the nozzle 16 through a distal end of the lumen 34. The nozzle 16 may also include a male luer connector 36 configured to connect to a female luer connector (not shown) of another fluid delivery device or fluid container (not shown) to established fluid communication between the syringe 10 and the fluid delivery device or container. The nozzle 16 can also include a threaded connector 38 including an annular body having threads on an interior surface thereof. The threads are configured to mate with corresponding threads of the fluid delivery device or fluid container to establish a more secure connection between the syringe 10 and the fluid delivery device or container.

The pump 14 can be a rotary valve-less piston pump configured to draw a precise discrete volume or dose of fluid from a fluid reservoir or fluid source, such as the interior volume 32, and to expel the precise volume or dose of the fluid through the nozzle 16 of the syringe 10. A valve-less piston pump does not include valves for controlling fluid flow through the pump and, instead, draws fluid into and expels fluid from the pump 14 by reciprocating motion of a piston 50. A rotary valve-less piston pump can refer to a pump which actuates a piston or similar pumping mechanism by rotational movement. As a result of the rotational movement, fluid is drawn through the pump without opening and closing of valves.

In some examples, the rotary valve-less piston pump 14 includes an annular body 40 defining a cavity 46 and having an open proximal end 42 and a closed distal end 44. The cavity 46 is in fluid communication with the interior volume 32 of the syringe barrel 12 and the lumen 34 of the nozzle 16. In some examples, the annular body 40 includes at least one, and preferably two or more, annular seal(s) 48 (shown in FIGS. 4A-4D) extending from an interior sidewall of the annular body 40.

In some examples, the piston 50 can be an elastomeric structure and the syringe barrel 12, annular body 40 of the pump 14, and nozzle 16 can be formed from a more rigid material (e.g., rigid plastic). The piston 50 can be any size and shape sufficient for drawing fluid through the cavity 46. For example, as shown in FIG. 4A, the piston 50 can be a substantially cylindrical structure including a proximal portion 52 having a first diameter D1 substantially similar to the diameter of the cavity 46 and configured to contact the annular seal(s) 48 of the annular body 40 and a recessed portion 54 having a smaller diameter D2 to draw fluid into and expel fluid from the cavity 46. For a conventional syringe, such as a 20 mL syringe, the first diameter D1 of the piston 50 can be from 2 mm to 8 mm.

The piston 50 can be moved through the cavity 46 by sliding the piston 50 into and out of the cavity (e.g., axial displacement of the piston 50), by rotating the piston 50 in the cavity 46, or by a combination of axial and rotational movement. Moving the piston 50 in the cavity 46 is intended to create suction force sufficient to draw fluid into the cavity 46 from the interior volume 32 of the syringe barrel 12. Continued movement of the piston 50 expels the fluid from the cavity 46 through the lumen 34 of the nozzle 16.

The pump 14 is shown with the piston 50 in different positions in FIGS. 4A-4D. In FIG. 4A, the piston 50 is in an initial or partially retracted position. In the initial or partially retracted position, the piston 50 is in the cavity 46 and spaced apart from both the lumen 34 of the nozzle 16 and from a fluid entry port 33 connected to the interior volume 32 of the syringe barrel 12. Neither the lumen 34 nor the fluid entry port 33 are sealed by the piston 50. In FIG. 4A, the recessed portion 54 of the piston 50 is shown facing the lumen 34 of the nozzle 16. However, in the partially retracted position, the recessed portion 54 can be provided in any orientation as long as fluid flow through the cavity 46 is permitted. In the partially retracted position, fluid is prevented from leaking from the open proximal end 42 of the annular body 40 due to a seal between the piston 50 and the annular seal(s) 48. When the piston 50 is in the partially retracted position, the syringe 10 can be used in a conventional manner. For example, fluid can be drawn into or expelled from the interior volume 32 of the syringe barrel 12 by advancing or retracting the plunger 24 through the syringe barrel 12. Generally, the syringe 10 will be initially provided to a user with the piston 50 in the partially retracted position, so that the user can fill the interior volume 32 of the syringe 10 with fluid using the plunger 24. In some examples, a cover (not shown) may be placed over the partially retracted piston 50 during shipping to prevent the piston 50 from moving during shipping and/or prior to use.

Figure 4B:
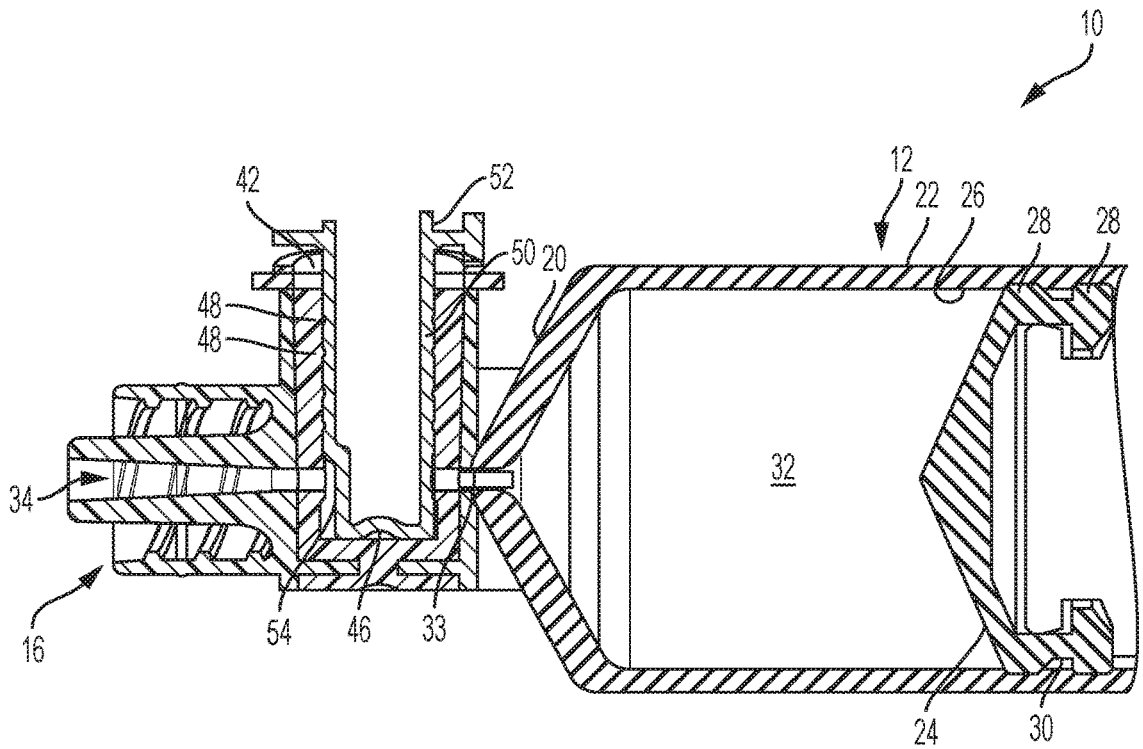
FIG. 4B is a cross-sectional view of the portion of the syringe of FIG. 1 shown in FIG. 4A in a seated or engaged position.
Figure 5:
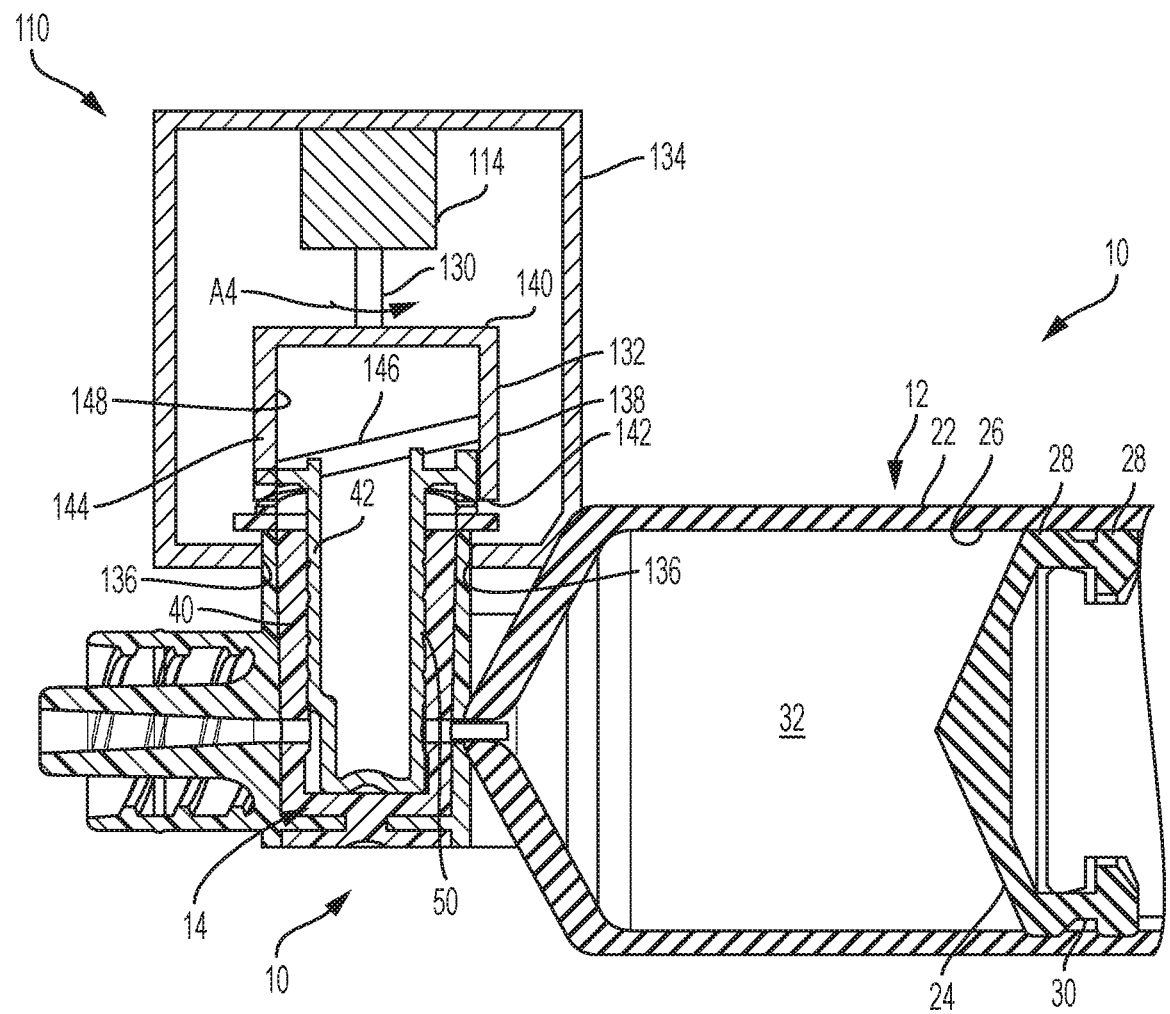
FIG. 5 is a cross-sectional view of a portion of the syringe of FIG. 1, connected to a drive unit for advancing and retracting a piston of the pump.

In order to attach a drive unit or similar motorized device to the piston 50 of the pump 14, the piston 50 is fully inserted into the cavity 46 to a seated or bottom-of-stroke position, as shown in FIG. 4B. In this position, the piston 50 is fully inserted into the cavity 46 and the recessed portion 54 faces the lumen 34 of the nozzle 16. Fluid flow from the cavity 46 through the lumen 34 is permitted. The piston 50 seals the fluid entry port 33. This orientation of the recessed portion 54 is necessary, so that fluid in the cavity 46 can be expelled from the pump 14 through the lumen 34 at the bottom of each piston stroke.

Figure 4C:
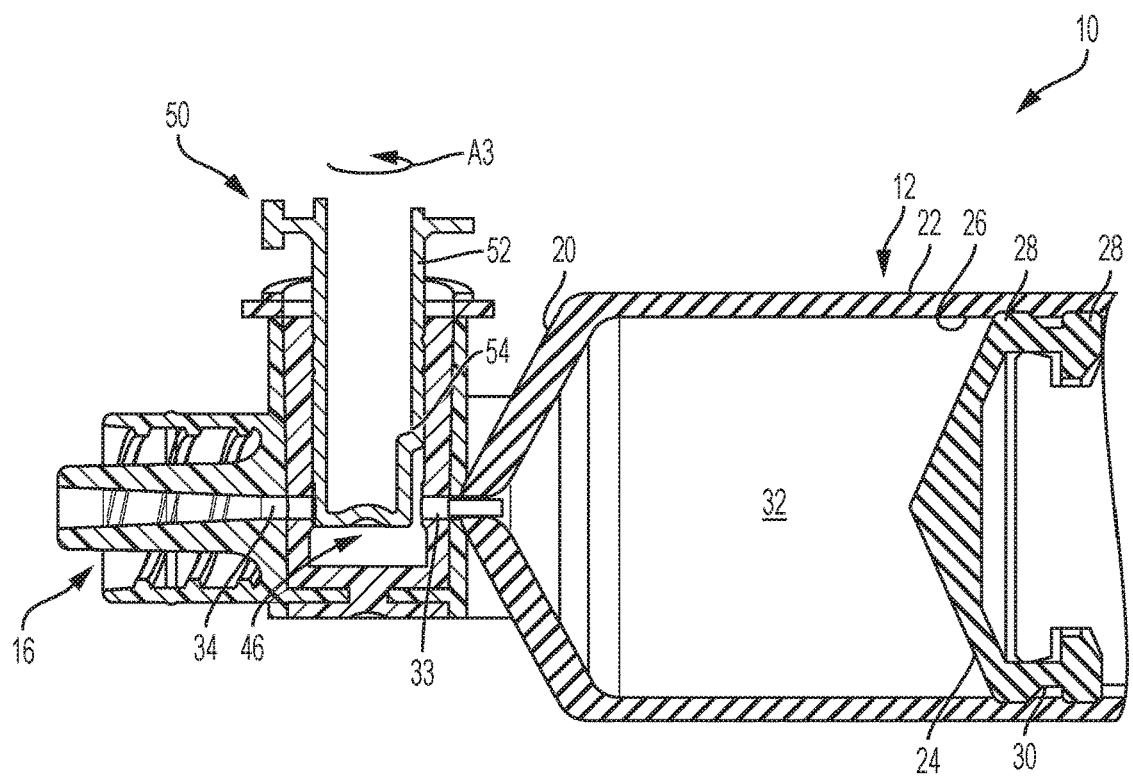
FIG. 4C is a cross-sectional view of the portion of the syringe of FIG. 1 shown in FIG. 4A in a suction or top of stroke position.

Actuating the drive unit or motorized device retracts the piston 50 in a direction of arrow A1 (shown in FIG. 4A) from the seated position to a suction or top-of-stroke position. Simultaneously, the piston 50 is rotated in a direction of arrow A3 a half turn or 180 degrees. The suction or top-of-stroke position is shown in FIG. 4C. Rotating the piston 50 the half turn causes the recessed portion 54 to transition from facing the lumen 34 and sealing the fluid entry port 33 (in FIG. 4B) to facing the fluid entry port 33 and sealing the lumen 34 (as shown in FIG. 4C). Once the piston 50 is rotated so that it no longer seals the fluid entry port 33, fluid flows from the interior volume 32 of the syringe barrel 12 into the cavity 46 due to a suction force generated by movement of the piston 50.

Figure 4D:
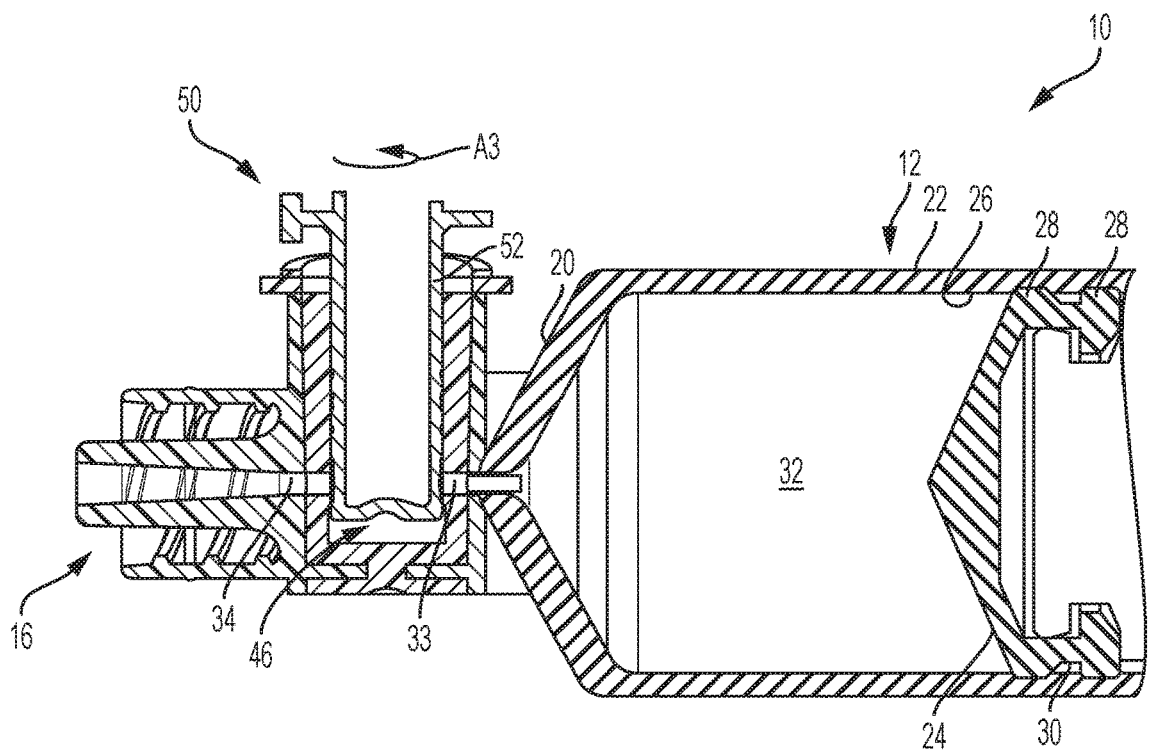
FIG. 4D is a cross-sectional view of the portion of the syringe of FIG. 1 shown in FIG. 4A in a cross-over or intermediate position.

As shown in FIG. 4D, the piston 50 is illustrated in a cross-over or intermediate position, in which the piston 50 seals both the fluid entry port 33 and the lumen 34. In order to advance the piston from the suction or top-of-stroke position (shown in FIG. 4C) to the intermediate or cross-over position (FIG. 4D), the piston 50 is advanced axially into the cavity 46 in a direction of arrow A2 (shown in FIG. 4A) and rotated in the direction of arrow A3. Continued rotational and axial movement of the piston 50 from the intermediate or cross-over position to the seated position (FIG. 4B) seals the fluid entry port 33 and opens the lumen 34. Once the lumen 34 is opened, a discrete dose or volume of fluid is expelled from the cavity 46 and into the lumen 34. As shown in FIGS. 4B and 4C, the piston 50 rotates a half turn (e.g., 180 degrees) between the top-of-stroke or suction position (FIG. 4C) and the seated position (FIG. 4B).

The piston 50 positions shown in FIGS. 4B to 4D illustrate a full stroke of the piston pump 14, in which the piston 50 moves axially from the seated position, to the suction position, and back to the seated position. The piston 50 rotates 360 degrees (e.g., a full rotation) during each piston stroke. Piston strokes can be repeatedly performed either manually or under power from an automated drive mechanism to draw a precise total volume of fluid from the interior volume 32 through the nozzle 16 as a series of discrete doses. For example, to manually operate the pump 14, a user may grasp a portion of the proximal end of the piston 50 for retraction and may press against the proximal end of the piston 50 to advance the piston 50 through the cavity 46. The user may also rotate or twist the piston 50, as described above.

In other examples, the pump 14 is actuated automatically by, for example, a motor, linear actuator, or similar powered device. An exemplary drive unit 110, which can be used with the pump 14, is shown in FIG. 5. The drive unit 110 includes, for example, a motor 114 configured to drive a shaft 130 and cam 132. The motor 114, shaft 130, and cam 132 can be contained in a housing 134 configured to be mounted to a portion of the syringe 10 and/or pump 14. For example, as shown in FIG. 5, the housing 134 can include a lower opening 136 configured to receive a top portion and/or open proximal end 42 of the annular body 40 of the pump 14. The lower opening 136 can include, for example, one or more latch members for engaging the pump 14 to mount the drive unit 110 to the pump 14. The motor 114 can be any suitable movement-generating device, such as a battery-powered electric motor. The motor 114 is configured to rotate the shaft 130 in a direction of arrow A4. Alternatively, the motor 114 may twist the shaft 130 back and forth. For example, the motor 114 could twist the shaft 180 degrees in one direction and then 180 degrees in an opposite direction.

As shown in FIG. 5, the shaft 130 is fixedly mounted to the cam 132. As will be appreciated by those skilled in the art, a variety of different camming structures can be used to impart axial and/or rotational movement to the piston 50 from rotating motion generated by the motor 114. For example, as shown in FIG. 5, the cam 132 includes a tubular body 138 having a closed first end 140 mounted to the shaft 130, an open second end 142 configured to receive the piston 50, and a sidewall 144 extending between the first and second ends thereof. The piston 50 is received within the tubular body 138. For example, a protruding portion of the piston 50 can be engaged by a track 146 extending radially outward from an inner surface 148 of the sidewall 144. Rotation of the cam 132 by the shaft 130 causes the piston 50 to travel along the track 146 from a distal end to a proximal end thereof. As the piston 50 travels through the track 146, the piston 50 moves through a piston stroke between the seated position (shown in FIG. 4B) and the suction position (FIG. 4C). In some examples, as described above, the track 146 can be sized, such that the piston 50 also rotates as it moves along the track 146, in addition to moving back and forth in an axial direction.

In use, actuation of the pump 14 expels a volume of fluid from the syringe barrel 12. For example, the syringe 10 and pump 14 can be provided to an end-user in a partially retracted position, as shown in FIG. 4A. The user draws fluid into the interior volume 32 of the syringe barrel 12 in a conventional manner. To actuate the pump 14, the piston 50 is manually or automatically pushed into the cavity 46 to seat the piston 50 in the cavity 46. The drive unit 110 is then connected to the pump 14 and actuated to perform at least one piston stroke. The volume of fluid per piston stroke can be an amount of fluid from about 5 mL to 100 mL. The process of retraction and seating of the piston 50 can be repeated multiple times to dispense additional volumes of fluid from the syringe barrel 12.

Fluid Delivery System

Figure 6:
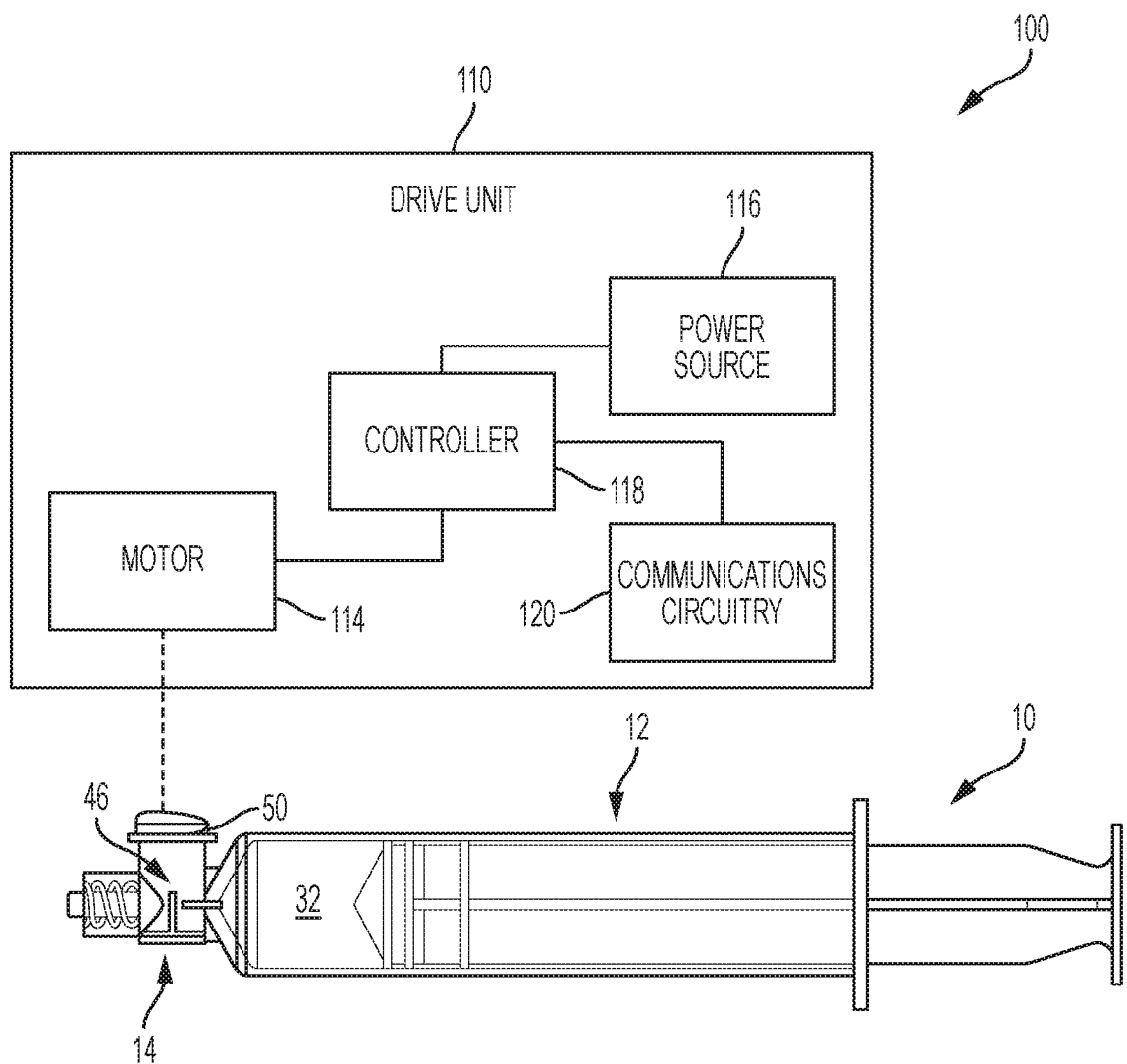
FIG. 6 is a schematic drawing of electrical components of a drive unit of a fluid delivery system including the syringe and valve-less pump of FIG. 1, according to an aspect of the disclosure.

In some examples, the syringe 10 and drive unit 110 can be integrated with a fluid delivery system 100. An exemplary fluid delivery system 100 including the syringe 10 and electronical components of the drive unit 110 is shown in FIG. 6. As shown in FIG. 6, the fluid delivery system 100 includes the syringe 10 having the syringe barrel 12, the pump 14, and the nozzle 16 (shown in FIGS. 1-4D).

The drive unit 110 can be connected to the pump 14 for actuating the pump 14 to draw fluid from the interior volume 32 of the syringe barrel 12. The drive unit 110 includes the motor 114, such as a battery powered electric motor and a power source 116, such as batteries for the motor 114 or a plug for connecting the system 100 to a standard wall outlet. The drive unit 110 can also include a controller 118 for controlling retraction and advancement of the piston 50 to dispense a desired fluid volume from the syringe 10 and communications circuitry 120 for receiving operating instructions from an external or remote source or device. For example, information confirming that a fluid volume has been dispensed from the syringe 10 may be sent to the remote source with the communications circuitry 118. The drive unit 110 can be re-usable. For example, after use, the syringe 10 including the pump 14 can be removed from the drive unit 110 and discarded. The multi-use drive unit 110 can then be removably connected to another syringe 10 for dispensing another fluid volume. In other examples, the drive unit 110 can be partially or completely disposable or can be refurbished after each use.

Methods for Dispensing Fluid with a Syringe and Pump

Figure 7:
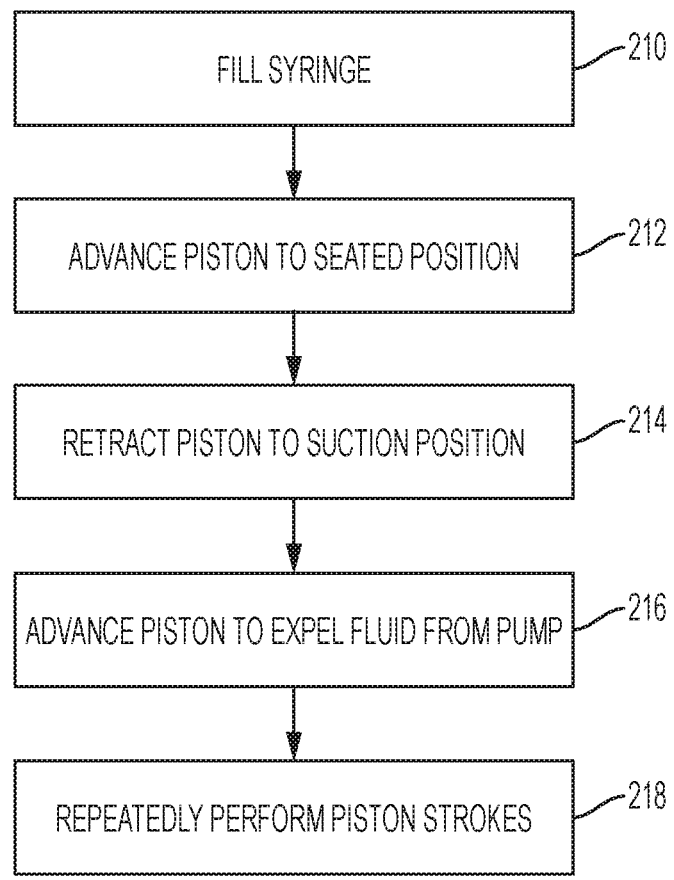
FIG. 7 is a flowchart illustrating steps for drawing fluid from a syringe including a pump according to an aspect of the disclosure.

According to another aspect of the disclosure, a method of dispensing fluid from a syringe is disclosed herein. With reference to FIG. 7, as shown in a first step 210, the method includes drawing fluid into the syringe barrel through a distal end of the nozzle to fill the syringe. Specifically, a user draws fluid into the syringe barrel by grasping a proximal end of a plunger rod connected to the plunger and pulling the plunger through the syringe barrel in the proximal direction. In order to draw fluid into the nozzle, the piston must be in its partially retracted position such that fluid communication from the nozzle lumen to the interior of the syringe barrel through the cavity of the pump is permitted and fluid does not leak past the piston and annular seal(s) of the annular body. After a desired amount of fluid is drawn into the syringe barrel, the syringe is ready to dispense fluid through the nozzle.

As shown in a second step 212, to perform an initial pump, the piston is advanced through the cavity of the pump to a seated position. When the piston is in the seated position, a drive unit or similar motorized device can be attached to the piston to automatically move the piston through the cavity. As shown in a third step at step 214, the pump piston is moved to a suction position. Specifically, the piston is moved in a proximal direction and rotated to draw fluid from the interior volume of the syringe barrel into the pump cavity. As shown in a fourth step 216, the piston is then advanced axially through the cavity in the distal direction, thereby expelling the fluid from the nozzle through the lumen. As shown in a fifth step 218, retracting and advancing the plunger can be repeatedly carried out to expel multiple precise volumes or doses of the fluid from the syringe.

2-Piece Syringe Assembly

According to another aspect of the disclosure, an assembly 300 for fluid delivery including a conventional syringe 310 and a pump assembly 314 removably connected to a distal end of the syringe 310, such as a 20 mL syringe including a luer connector, is provided. The syringe 310 can be a conventional fluid-dispensing syringe including a syringe barrel 312 having an open proximal end 318, a closed distal end 320, and a sidewall 322 extending therebetween. As in previously described examples, a plunger 324 and attached plunger rod 362 can be inserted in and slidably sealed to an internal surface of the syringe barrel 312. For example, the plunger 324 can include an annular seal 328 extending from a sidewall 322 of the plunger 324, which is configured to press against the sidewall of the syringe barrel to form a sufficient seal. The plunger 324 can be configured to move through the barrel 312 in the proximal and distal directions to draw fluid into the syringe barrel 312 or to expel fluid therefrom. The syringe 310 also includes a nozzle 316 extending from the closed distal end 320 of the syringe barrel 312. The nozzle 316 includes a lumen 334 extending longitudinally therethrough in fluid communication with an interior volume 332 of the syringe barrel 312. The nozzle 316 can include a connector, such as a male luer connector 336, for mounting the syringe 310 to a corresponding connector (e.g., a female luer connector 366) of the pump assembly 314. Desirably, the female luer connector 366 of the pump assembly 314 is a standard dimension configured to mount to a wide variety of commercially available syringes.

The pump assembly 314 can be removably connected to the nozzle 316 of the syringe 310 and in fluid communication with the interior volume 332 of the syringe barrel 312 through the lumen 334 of the nozzle 316 and a cavity 346 of the pump assembly 314. As in previously described examples, the pump assembly 314 is configured to draw fluid from the syringe barrel 312 and to dispense the received fluid. For example, the pump assembly 314 may include an annular body 340 having an open proximal end 342 and a closed distal end 344, which define the cavity 346. The pump assembly 314 can further include a piston 350 slidably inserted in the cavity 346. The pump assembly 314 is configured to draw fluid from the interior volume 332 of the syringe barrel 312 into the cavity 346 through a fluid entry or inflow port 358 coupled to the female luer connector 366. Fluid is expelled from the cavity 346 through an outflow port 360. In some examples, the outflow port 360 includes a male luer connector 336 or similar connecting structure for connecting the pump assembly 314 to another fluid delivery device or fluid container.

In use, a user obtains a conventional syringe 310 and connects the pump assembly 314 to the distal end of the syringe 310 by, for example, inserting the male luer connector 336 of the syringe nozzle 316 into the corresponding female luer connector 366 of the pump assembly 314. With the piston 350 of the pump assembly 314 in the partially retracted position, the user draws fluid into the syringe 310 by moving the plunger rod 362 and plunger 324 in the proximal direction through the syringe barrel 312. After the syringe barrel 312 is filled or partially filled, fluid is expelled from the syringe 310 by pumping the pump assembly 314 in the manner described hereinabove. Specifically, as previously described, retracting and advancing the piston 350 of the pump assembly 314 draws fluid from the syringe barrel 312 and expels the fluid through the outflow port 360 of the pump assembly 314. After fluid dispensing is completed, the pump assembly 314 can be removed from the syringe 310 and either discarded or cleaned for reuse.

Although the invention has been described in detail for the purpose of illustration based on what is currently considered to be the most practical and preferred embodiments or aspects, it is to be understood that such detail is solely for that purpose and that the invention is not limited to the disclosed embodiments or aspects, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A syringe comprising:
a syringe barrel comprising an open proximal end, a closed distal end, and a sidewall extending therebetween;
a plunger having an annular sidewall configured to seal against an interior surface of the sidewall of the syringe barrel, the plunger being configured to move through the syringe barrel in proximal and distal directions;
a rotary valve-less piston pump directly connected to and in fluid communication with an interior volume of the syringe barrel configured to draw fluid from the syringe barrel by rotation of a piston, the rotary valve-less piston pump comprising an annular body having an open proximal end and a closed distal end, which define a cavity, the cavity being in fluid communication with the interior volume of the syringe barrel and a lumen of a nozzle, wherein the annular body comprises at least one annular seal extending from an interior sidewall thereof, the seal being configured to prevent fluid from leaking from the open proximal end of the annular body; and
the nozzle comprising the lumen aligned and directly connected with the nozzle and in fluid communication with the rotary valve-less piston pump configured to receive fluid drawn from the syringe barrel by the pump and to expel the fluid through a distal end of the lumen, such that the fluid flows from the syringe barrel to the rotary valve-less piston pump and then to a distal end of the nozzle, the rotary valve-less piston pump connected between the syringe barrel and the nozzle,
a drive unit connected to the pump for actuating the pump to draw fluid from the interior volume of the syringe barrel, the drive unit comprising a motor, a rotating shaft, a track, a linear actuator, and a cam, wherein rotation of the cam by the shaft causes the piston to travel along the track,
wherein the piston is slidably rotatably inserted in the cavity,
wherein, when the piston is in a partially retracted position during use, fluid flow between the lumen of the nozzle and the interior volume of the syringe barrel through the cavity of the pump is permitted, such that the fluid comes in contact with a bottom surface of the piston, and
wherein movement of the plunger in the distal direction allows the expel of the fluid through the distal end of the lumen and the nozzle, the lumen, and the direction of the movement of the plunger are coaxial.

2. The syringe of claim 1, wherein, when the piston is in a partially retracted position, fluid flow through the open proximal end of the annular body is prevented.

3. The syringe of claim 2, wherein movement of the piston in an axial direction into the cavity from the partially retracted position causes the piston to seal at least one of the lumen of the nozzle or the interior volume of the syringe barrel, such that fluid communication between the cavity and the nozzle and/or the syringe barrel is prevented.

4. The syringe of claim 1, wherein, during a piston stroke, the piston rotates 360 degrees and moves axially through the cavity between a seated position, a suction position, and back to the seated position.

5. The syringe of claim 4, wherein in the suction position, fluid is drawn from the interior of the syringe barrel into the cavity and, wherein, in the seated position, fluid is expelled from the cavity through the lumen of the nozzle.

6. The syringe of claim 1, wherein the nozzle further comprises a male luer connector configured to connect to a female luer connector of another fluid delivery device to establish fluid communication between the syringe and the fluid delivery device.

7. The syringe of claim 1, wherein the nozzle further comprises a threaded connector comprising an annular body having threads on an interior surface thereof.

8. The syringe of claim 1, wherein the pump is integrally molded to the syringe barrel.

9. The syringe of claim 1, wherein the pump is removably connected to the syringe barrel.

10. A syringe assembly for delivery of a fluid, comprising:
a syringe comprising a syringe barrel comprising an open proximal end, a closed distal end, and a sidewall extending therebetween; a plunger disposed in the syringe barrel having an annular sidewall configured to seal an interior surface of the sidewall of the syringe barrel and configured to move through the syringe barrel in proximal and distal directions; and a nozzle extending from the distal end of the syringe barrel comprising a lumen in fluid communication with an interior volume of the syringe barrel; and a pump assembly removably and directly connected to the nozzle of the syringe barrel in fluid communication with the interior volume of the syringe barrel, the pump assembly comprising a rotary piston pump configured to draw fluid from the interior volume of the syringe barrel through an inflow port of the pump assembly and to expel the received fluid from an outflow port thereof by rotational movement of a piston, a drive unit connected to the pump for actuating the pump to draw fluid from the interior volume of the syringe barrel, the drive unit comprising a motor, a rotating shaft, a track, a linear actuator, and a cam, wherein rotation of the cam by the shaft causes the piston to travel along the track, wherein the rotary piston pump comprises a rotary valve-less piston pump comprising an annular body having an open proximal end and a closed distal end, which define a cavity, wherein the piston is slidably inserted into the cavity, wherein the fluid is drawn from the interior volume of the syringe barrel into the cavity through the inflow port and is expelled from the cavity through the outflow port into the nozzle, such that the fluid comes into contact with a bottom surface of the rotary piston pump in the cavity, after which the fluid is expelled through the outflow port, wherein to permit fluid flow between the lumen of the nozzle and the interior volume of the syringe barrel through the cavity of the pump during use to allow for fluid to be drawn with the plunger, the piston is in a partially retracted position such that the fluid comes in contact with a bottom surface of the piston, and wherein movement of the plunger in the distal direction allows the expel of the fluid through the distal end of the lumen and the inflow port, the outflow port, and the direction of the movement of the plunger are axially aligned.

11. The assembly of claim 10, wherein, when the piston is in a partially retracted position, fluid flow through the open proximal end of the annular body is prevented.

12. The assembly of claim 11, wherein movement of the piston in an axial direction from the partially retracted position into the cavity causes the piston to seal at least one of the inflow port or the outflow port, such that fluid communication between the cavity and the inflow port and/or the outflow port is prevented.

13. The assembly of claim 10, wherein, during a piston stroke, the piston rotates 360 degrees and moves axially through the cavity between a seated position, a suction position, and back to the seated position.

14. A fluid delivery system, comprising:
a syringe comprising:
a syringe barrel comprising an open proximal end, a closed distal end, and a sidewall extending therebetween;
a plunger comprising an annular sidewall configured to seal against an interior surface of the sidewall of the syringe barrel and configured to move through the syringe barrel in proximal and distal directions;
a rotary valve-less piston pump directly connected to and in fluid communication with an interior volume of the syringe barrel configured to draw fluid from the syringe barrel by rotational movement of a piston, the rotary valve-less piston pump comprising an annular body having an open proximal end and a closed distal end, which define a cavity, the cavity being in fluid communication with the interior volume of the syringe barrel and a lumen of a nozzle; and
the nozzle comprising the lumen aligned and rigidly connected with the nozzle and in fluid communication with the pump and configured to receive fluid drawn from the syringe barrel by the pump and to expel the fluid through a distal end of the lumen, such that the fluid flows from the syringe barrel to the rotary valve-less piston pump and then to a distal end of the nozzle, the rotary valve-less piston pump connected between the syringe barrel and the nozzle; and
a drive unit connected to the pump for actuating the pump to draw fluid from the interior volume of the syringe barrel, the drive unit comprising a motor, a rotating shaft, a track, a linear actuator, and a cam, wherein rotation of the cam by the shaft causes the piston to travel along the track,
wherein the piston is slidably rotatably inserted into the cavity,
wherein, to permit fluid flow between the lumen of the nozzle and the interior volume of the syringe barrel through the cavity of the pump during use, the piston is in a partially retracted position such that the fluid comes in contact with a bottom surface of the piston, and
wherein movement of the plunger in the distal direction allows the expel of the fluid through the distal end of the lumen and the nozzle, the lumen, and the direction of the movement of the plunger are coaxial.

* * * * *